(12) United States Patent
Stricko, III et al.

(10) Patent No.: US 11,944,265 B2
(45) Date of Patent: Apr. 2, 2024

(54) MEDICAL IMAGING SYSTEMS AND METHODS

(71) Applicant: Intuitive Surgical Operations, Inc., Sunnyvale, CA (US)

(72) Inventors: Robert G. Stricko, III, San Francisco, CA (US); Jacob L. Divone, Mountain View, CA (US); Glenn C. Stante, San Francisco, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 902 days.

(21) Appl. No.: 16/993,893

(22) Filed: Aug. 14, 2020

(65) Prior Publication Data
US 2021/0045618 A1 Feb. 18, 2021

Related U.S. Application Data

(60) Provisional application No. 62/888,244, filed on Aug. 16, 2019.

(51) Int. Cl.
*A61B 1/00* (2006.01)
*A61B 1/06* (2006.01)
*G02B 30/20* (2020.01)
*G06T 7/00* (2017.01)

(52) U.S. Cl.
CPC ........ *A61B 1/00096* (2013.01); *A61B 1/0005* (2013.01); *A61B 1/0676* (2013.01); *G02B 30/20* (2020.01); *G06T 7/0012* (2013.01); *G06T 2207/10068* (2013.01)

(58) Field of Classification Search
CPC . A61B 1/00096; A61B 1/0005; A61B 1/0676; G02B 30/20; G02B 30/22; G06T 7/0012; G06T 2207/10068

USPC ........ 600/190, 109, 111, 112, 138, 160, 166, 600/178, 179
See application file for complete search history.

(56) References Cited

U.S. PATENT DOCUMENTS 10,646,283 B2 * 5/2020 Johnson .................. G06F 3/011
11,553,969 B1 * 1/2023 Lang ..................... G06T 7/0012
(Continued)

FOREIGN PATENT DOCUMENTS

WO WO-2009134634 A2 * 8/2023 ............. A61B 1/018

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Eduardo C Robert
*Assistant Examiner* — David C Comstock

(57) ABSTRACT

An exemplary medical imaging system includes an imaging device that includes a visible light camera configured to obtain image data representative of a two-dimensional visible light image of a scene and a depth sensor separate from the visible light camera and configured to obtain depth data representative of a depth map of the scene. The medical imaging system further includes a image processing system communicatively coupled to the imaging device and configured to generate, based on the image data and the depth data, a right-side perspective image of the scene and a left-side perspective image of the scene that together form a stereoscopic image of the scene.

18 Claims, 11 Drawing Sheets

(56) References Cited

U.S. PATENT DOCUMENTS

2006/0069314 A1* 3/2006 Farr .................. A61B 1/0653
                                                600/179
2019/0231220 A1* 8/2019 Refai .................. H04N 13/25
2020/0281454 A1* 9/2020 Refai .................. A61B 90/39

* cited by examiner

MEDICAL IMAGING SYSTEMS AND METHODS

RELATED APPLICATIONS

The present application claims priority to U.S. Provisional Patent Application No. 62/888,244, filed on Aug. 16, 2019, and entitled "MEDICAL IMAGING SYSTEMS AND METHODS," the contents of which are hereby incorporated by reference in their entirety.

BACKGROUND INFORMATION

During a medical procedure performed within an internal space of a patient, an imaging device (e.g., an endoscope) may capture and provide a view of tissue and/or other structures within the internal space. In some examples, it may be desirable for a user (e.g., a surgeon) to perform actions associated with the internal space depicted by the internal view provided by the imaging device. For instance, during a minimally invasive surgical procedure, it may be desirable to insert and manipulate various surgical instruments, supplies, or the like within the internal space in such a way that the inserted instruments and supplies are readily seen and easily used by the user looking at the internal view provided by the imaging device.

Conventional imaging devices used during medical procedures include one or more visible light cameras configured to capture visible light images (e.g., color images) of a scene. However, using conventional imaging devices during a medical procedure may have certain drawbacks. For example, a conventional imaging device may produce reflection, glare, and/or shadows within the internal space. These artifacts may make it difficult for a user to perceive depth within the images captured by the conventional imaging device and/or for conventional visible light image-based techniques to generate an accurate depth map of the internal space. This, in turn, may complicate some types of procedures performed by the user and/or otherwise introduce inefficiencies and/or inconveniences.

SUMMARY

The following description presents a simplified summary of one or more aspects of the systems and methods described herein. This summary is not an extensive overview of all contemplated aspects and is intended to neither identify key or critical elements of all aspects nor delineate the scope of any or all aspects. Its sole purpose is to present one or more aspects of the systems and methods described herein as a prelude to the detailed description that is presented below.

An exemplary medical imaging system includes an imaging device that includes a visible light camera configured to obtain image data representative of a two-dimensional visible light image of a scene, and a depth sensor separate from the visible light camera and configured to obtain depth data representative of a depth map of the scene; and a image processing system communicatively coupled to the imaging device and configured to generate, based on the image data and the depth data, a right-side perspective image of the scene and a left-side perspective image of the scene that together form a stereoscopic image of the scene.

An exemplary system includes an imaging device comprising a visible light camera configured to obtain image data representative of a two-dimensional visible light image of a scene, and a depth sensor configured to obtain depth data representative of a depth map of the scene; a image processing system communicatively coupled to the imaging device and configured to generate, based on the image data and the depth data, a right-side perspective image of the scene and a left-side perspective image of the scene that together form a stereoscopic image of the scene; and a user control system communicatively coupled to the image processing system and configured to facilitate remote performance by a user of a medical procedure with respect to a patient, the user control system comprising a stereoscopic viewer that comprises: a first display device configured to display the right-side perspective image of the scene, and a second display device configured to display the left-side perspective image of the scene.

An exemplary imaging device comprises a visible light camera configured to obtain image data representative of a two-dimensional visible light image of a scene and a depth sensor separate from the visible light camera and configured to obtain depth data representative of a depth map of the scene.

An exemplary method includes obtaining, using a visible light camera included within an imaging device, image data representative of a two-dimensional visible light image of a scene; obtaining, using a depth sensor included within the imaging device, depth data representative of a depth map of the scene; and generating, using a image processing system and based on the image data and the depth data, a right-side perspective image of the scene and a left-side perspective image of the scene that together form a stereoscopic image of the scene.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Medical imaging systems and methods are described herein. As will be described in more detail below, an exemplary medical imaging system includes an imaging device and an image processing system communicatively coupled to the imaging device. The imaging device includes a visible light camera configured to obtain image data representative of a two-dimensional visible light image of a scene (i.e., a two-dimensional image generated by detecting visible light reflecting off surfaces within the scene), and a depth sensor separate from the visible light camera and configured to obtain depth data representative of a depth map of the scene. The image processing system is configured to generate, based on the image data and the depth data, a right-side perspective image of the scene and a left-side perspective image of the scene that together form a stereoscopic image of the scene. These right and left-side perspective images may be displayed by respective display devices (e.g., display devices included in a stereoscopic viewer utilized by a surgeon to visualize the scene).

Various advantages and benefits are associated with the medical imaging systems and methods described herein. For example, by using a depth sensor separate from the visible light camera to generate depth data, a stereoscopic (i.e., three-dimensional) image of a scene may be rendered using a single visible light camera in combination with the depth sensor. This may obviate the need to have two visible light cameras within an imaging device (e.g., an endoscope) to generate a stereoscopic image of a scene, which may facilitate design and manufacture of stereoscopic imaging devices that are smaller, alternatively shaped, more flexible, and/or more precise compared to conventional stereoscopic imaging devices that have two visible light cameras.

Moreover, depth data obtained by depth sensor separate from a visible light camera may not be affected by reflection, glare, shadows, and/or other artifacts within an internal space of a patient. Accordingly, depth data obtained by such a depth sensor may be more accurate than depth data obtained using conventional visible light image-based techniques. This, in turn, facilitate more accurate and effective surgical operations that depend on depth data, as described in more detail herein.

Figure 1:
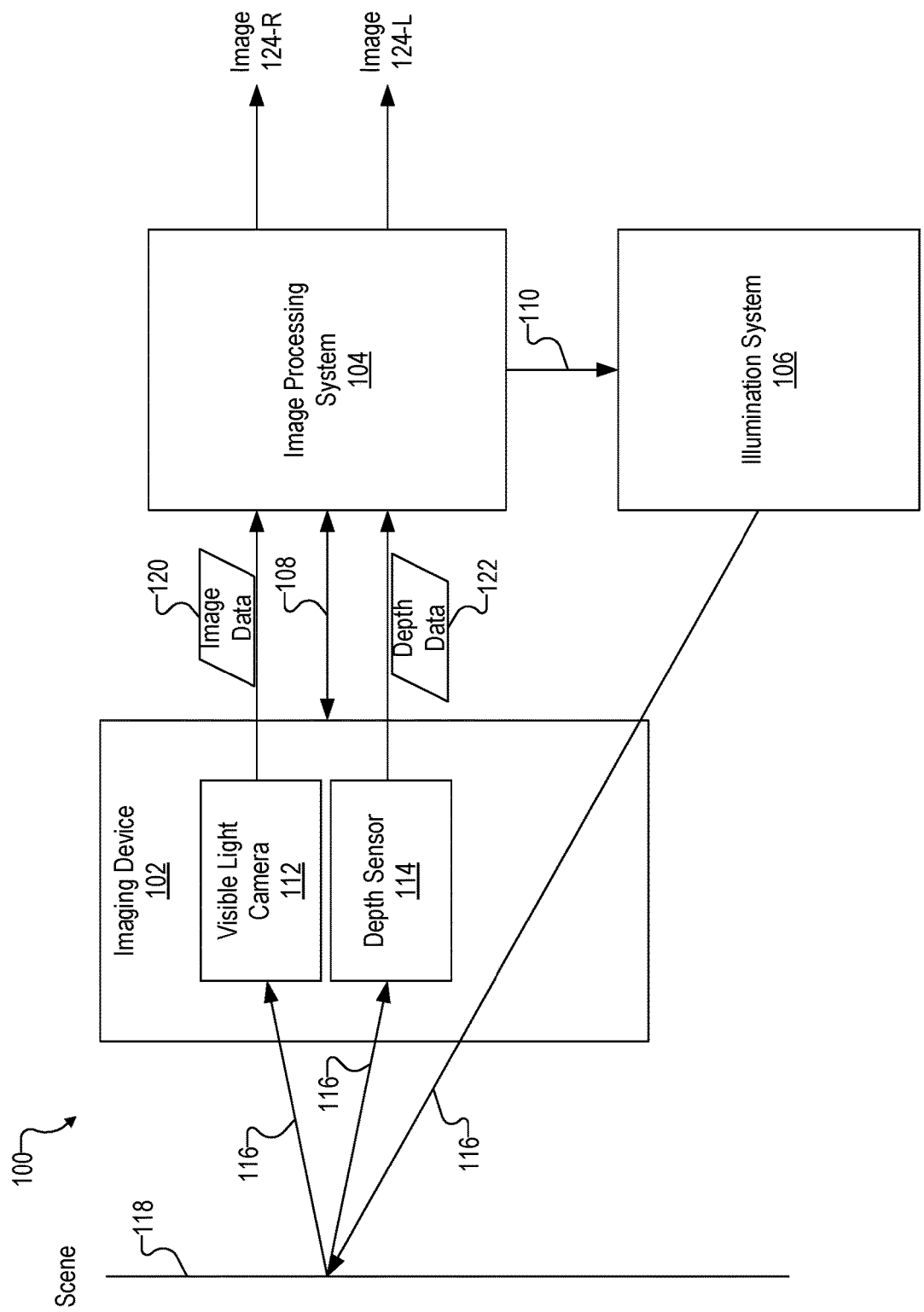
FIG. 1 illustrates an exemplary medical imaging system according to principles described herein.

FIG. 1 illustrates an exemplary medical imaging system 100 configured to capture images of a scene. In some examples, the scene may include a surgical area associated with a patient. The surgical area may, in certain examples, be entirely disposed within the patient and may include an area within the patient at or near where a surgical procedure is planned to be performed, is being performed, or has been performed. For example, for a minimally invasive surgical procedure being performed on tissue internal to a patient, the surgical area may include the tissue, anatomy underlying the tissue, as well as space around the tissue where, for example, surgical instruments used to perform the surgical procedure are located. In certain example implementations, the surgical area entirely disposed within the patient may be referred to as an "internal space". As described herein, any internal anatomy of the patient (e.g., vessels, organs, and/or tissue) and/or surgical instruments located in the internal space may be referred to as objects and/or structures.

As shown, medical imaging system 100 includes an imaging device 102, an image processing system 104, and an illumination system 106. While these are illustrated as separate components in FIG. 1, it will be recognized they may be combined in any suitable manner. For example, various aspects of illumination system 106 may be incorporated into imaging device 102 and/or image processing system 104. As another example, various aspects of image processing system 104 may be incorporated into imaging device 102.

Medical imaging system 100 may include additional or alternative components as may serve a particular implementation. For example, medical imaging system 100 may include various optical and/or electrical signal transmission components (e.g., wires, cables, lenses, optical fibers, choke circuits, waveguides, etc.).

As shown, image processing system 104 is communicatively coupled to imaging device 102 by way of a bidirectional communication link 108, which may be implemented using any suitable wired and/or wireless communication medium as may serve a particular implementation. Image processing system 104 is also communicatively coupled to illumination system 106 by way of a communication link 110, which may also be implemented using any suitable wired and/or wireless communication medium as may serve a particular implementation.

Imaging device 102 may be implemented by an endoscope or other camera device configured to capture images of a scene. As shown, imaging device 102 includes a visible light camera 112 ("camera 112") and a depth sensor 114. Camera 112 may be implemented by any suitable image sensor, such as a charge coupled device ("CCD") image sensor, a complementary metal-oxide semiconductor ("CMOS") image sensor, or the like. Depth sensor 114 may be implemented by one or more photodetectors (e.g., one or more single photon avalanche diode ("SPAD") detectors), CCD sensors, CMOS sensors, and/or any other suitable configuration configured to obtain depth data of a scene.

Image processing system 104 may be implemented by any suitable combination of hardware and/or software. For example, image processing system 104 may be implemented by one or more components included in a computer-assisted surgical system, as described herein.

In some examples, image processing system 104 may be configured to control an operation of imaging device 102 (e.g., by controlling an operation of camera 112 and depth sensor 114). For example, image processing system 104 may include one or more camera control units ("CCUs") configured to control various parameters (e.g., activation times, auto exposure, etc.) of camera 112 and/or depth sensor 114.

Image processing system 104 may additionally or alternatively be configured to provide operating power for components included in imaging device 102. For example, while imaging device 102 is communicatively coupled to image processing system 104, image processing system 104 may transmit operating power to camera 112 and depth sensor 114 in the form of one or more power signals.

Image processing system 104 may additionally or alternatively be configured to use imaging device 102 and illumination system 106 to generate stereoscopic images of a scene. This will be described in more detail below.

Illumination system 106 may be configured to emit light 116 (e.g., at the direction of image processing system 104) used to illuminate a scene to be imaged by imaging device 102. The light 116 emitted by illumination system 106 may include visible light and/or non-visible light (e.g., infrared light). As shown, light 116 may travel to the scene through imaging device 102 (e.g., by way of an illumination channel within imaging device 102 that may be implemented by one or more optical fibers, light guides, lenses, etc.). Various implementations and configurations of illumination system 106 are described herein.

As shown, light 116 emitted by illumination system 106 may reflect off a surface 118 within a scene being imaged by imaging device 102. Visible light camera 112 and depth sensor 114 may each detect the reflected light 116. Visible light camera 112 may be configured to generate, based on the detected light, image data 120 representative of a two-dimensional visible light image of the scene including surface 118. Depth sensor 114 may be configured to generate, based on the detected light, depth data 122. Image data 120 and depth data 122 may each have any suitable format.

To generate a stereoscopic image of a scene, image processing system 104 may direct illumination system 106 to emit light 116. Image processing system 104 may also activate (e.g., turn on) visible light camera 112 and depth sensor 114. Light 116 travels to the scene and reflects off of surface 118 (and, in some examples, one or more other surfaces in the scene). Camera 112 and depth sensor 114 both detect the reflected light 116.

Camera 112 (and/or other circuitry included in imaging device 102) may generate, based on detected light 116, image data 120 representative of a two-dimensional visible light image of the scene. This may be performed in any suitable manner. Visible light camera 112 (and/or other circuitry included imaging device 102) may transmit image data 120 to image processing system 104. This may also be performed in any suitable manner.

Depth sensor 114 may generate, based on detected light 116, depth data 122 representative of a depth map of the scene (e.g., a depth map of surface 118). This may be performed in any suitable manner.

For example, depth sensor 114 may be implemented by a time-of-flight sensor configured to measure an amount of time that it takes for a photon of light 116 to travel from illumination system 106 to depth sensor 114. Based on this amount of time, the time-of-flight sensor may determine a depth of surface 118 relative to a position of depth sensor 114. Data representative of this depth may be represented in depth data 120 in any suitable manner. For example, the depth map represented by depth data 120 may include an array of depth values (e.g., Z-buffer values) corresponding to each pixel in an image.

As another example, depth sensor 114 may be implemented by a structured light sensor configured to detect a reflection of light 116 that is in the form of a line of illumination that appears distorted from other perspectives than that of a projector or source of the light. Based on this detected line of illumination, the structured light sensor may determine a depth of surface 118 relative to a position of depth sensor 114. Data representative of this depth may be represented in depth data 120 in any suitable manner. For example, the depth map represented by depth data 120 may include an array of depth values (e.g., Z-buffer values) corresponding to each pixel in an image.

As another example, depth sensor 114 may be implemented by a interferometer and/or any other suitable sensor separate from (i.e., physically distinct from) visible light camera 112 that may be configured to determine a depth of a surface within a scene being imaged by imaging device 102.

Depth sensor 114 (and/or other circuitry included imaging device 102) may transmit depth data 122 to image processing system 104. This may be performed in any suitable manner.

Image processing system 104 may receive image data 120 and depth data 122 and perform one or more processing operations on the data to generate a right-side perspective image 124-R of the scene and a left-side perspective image 124-L representative of the scene. Exemplary ways in which images 124-R and 124-L may be generated based on image data 120 and depth data 122 are described herein. Image processing system 104 may then direct display devices to concurrently display images 124-R and 124-L in a manner that forms a stereoscopic image of the scene. Examples of this are provided herein.

Figure 2:
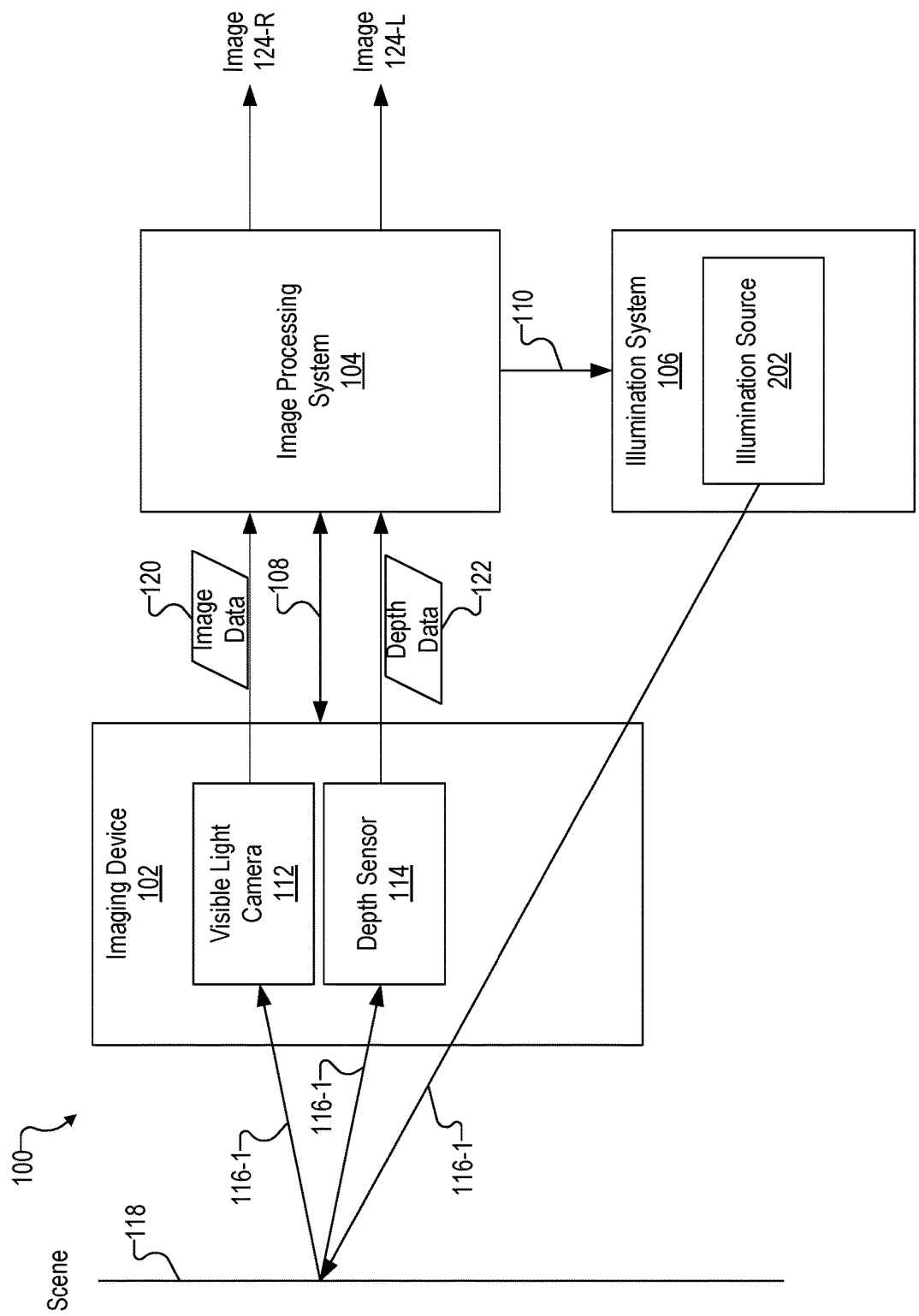
FIGS. 2-4 show exemplary implementations of a medical imaging system according to principles described herein.

FIG. 2 shows an exemplary implementation of medical imaging system 100 in which illumination system 106 is implemented by a single illumination source 202. Illumination source 202 may be configured to emit visible light 116-1.

Visible light 116-1 may include one or more color components. For example, visible light 116-1 may include white light that includes a full spectrum of color components (e.g., red, green, and blue color components). The red color component has wavelengths between approximately 635 and 700 nanometers ("nm"). The green color component has wavelengths between approximately 520 and 560 nm. The blue color component has wavelengths between approximately 450 and 490 nm.

In some examples, visible light 116-1 is biased to include more of one color component than another color component. For example, visible light 116-1 may be blue-biased by including more of the blue color component than the red and green color components.

In the implementation of FIG. 2, depth sensor 114 is configured to also detect visible light 116-1. Accordingly, the same illumination source 202 may be used for both camera 112 and depth sensor 114.

Figure 3:
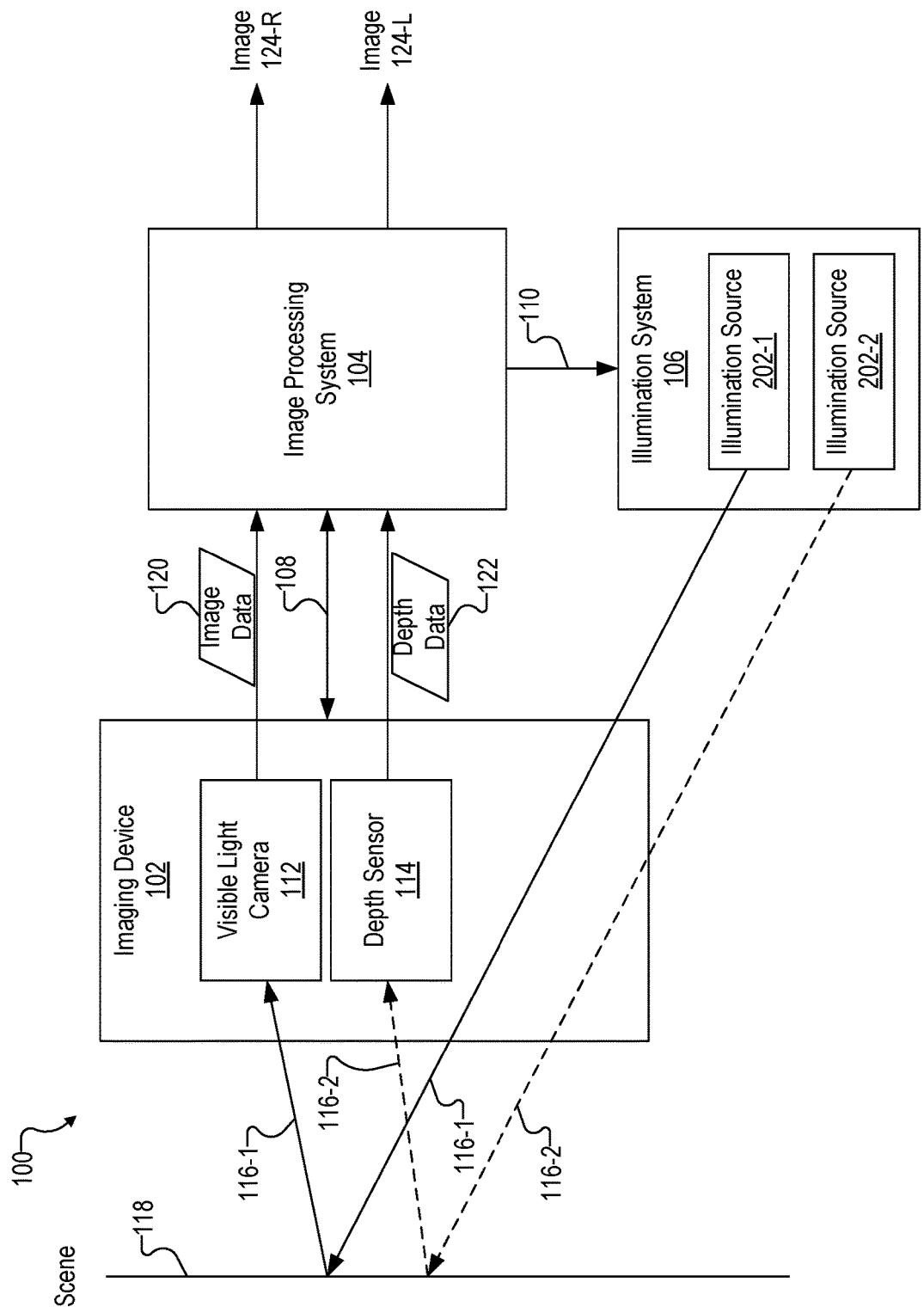

FIG. 3 illustrates an exemplary implementation of medical imaging system 100 in which illumination system 106 is implemented by separate illumination sources 202-1 and 202-2. In this implementation, illumination source 202-1 is configured to emit visible light 116-1 that is detected by camera 112. Illumination source 202-2 is configured to emit light 116-2 that reflects from surface 118 and is detected by depth sensor 114. In some examples, light 116-2 is non-visible light, such as infrared light. By having separate illumination sources 202 for camera 112 and depth sensor 114, camera 112 and depth sensor 114 may be configured to operate independently.

Figure 4:
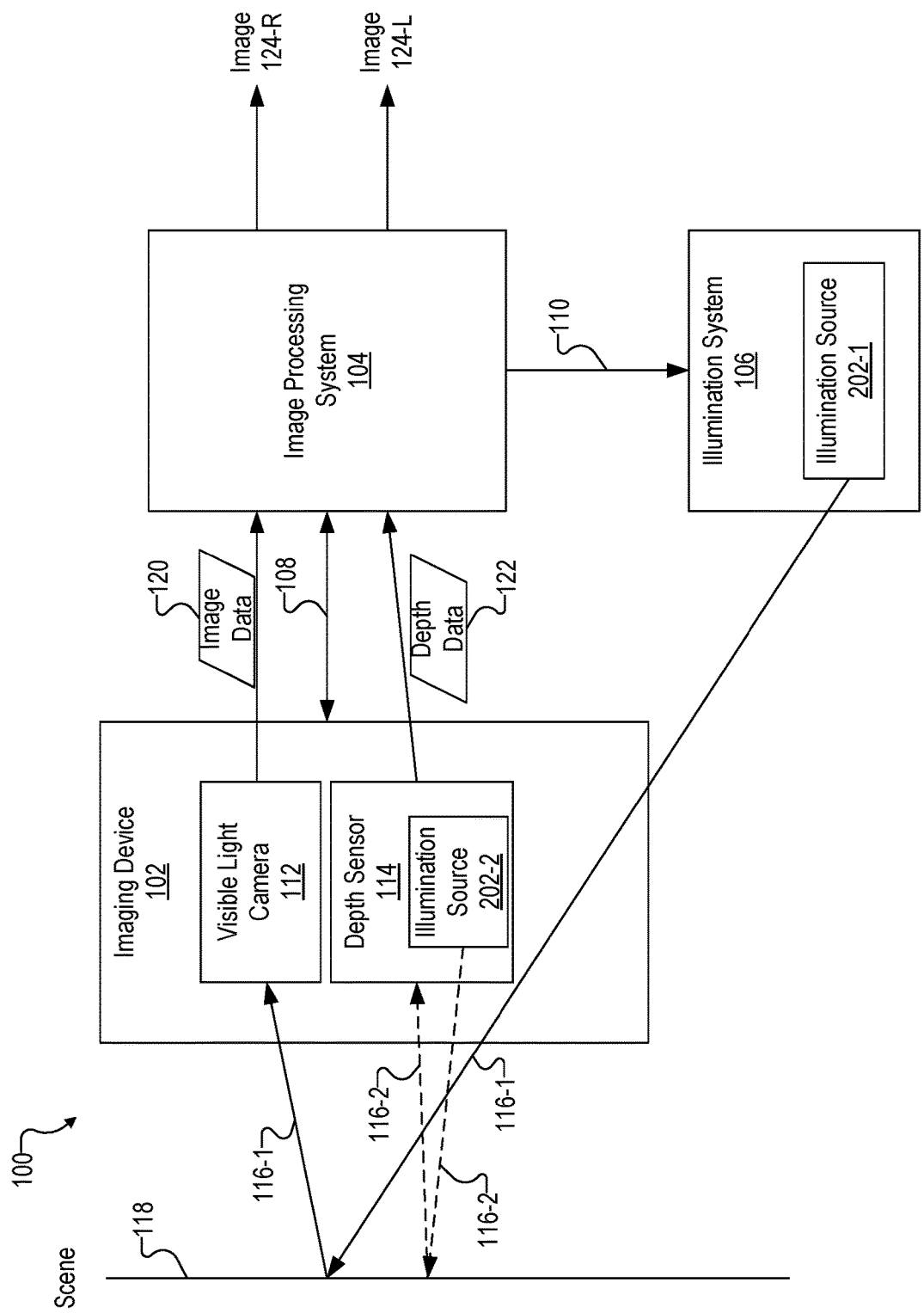

FIG. 4 illustrates an exemplary implementation of medical imaging system 100 in which illumination source 202-2 is integrated into depth sensor 114. In this implementation, image processing system 104 may control (e.g., activate) illumination source 202-2 by transmitting instructions to depth sensor 114.

Figure 5:
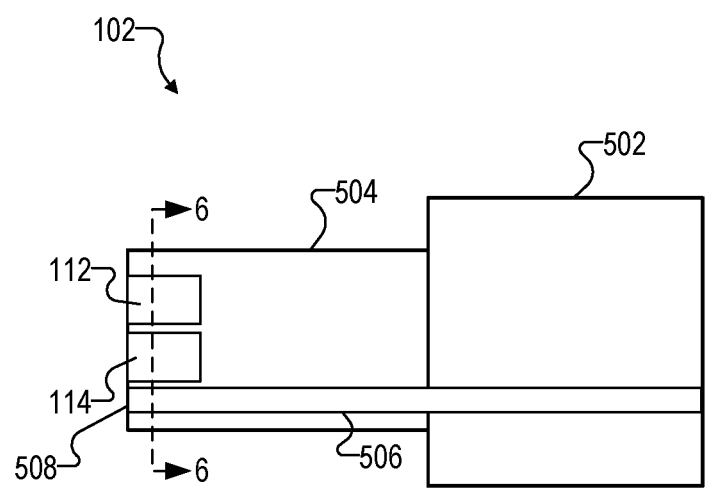
FIG. 5 illustrates an exemplary structural implementation of an imaging device according to principles described herein.

FIG. 5 illustrates an exemplary structural implementation of imaging device 102. As shown, imaging device 102 includes a camera head 502 and a shaft 504 coupled to and extending away from camera head 502. Camera head 502 and shaft 504 together implement a housing of imaging device 102. Imaging device 102 may be manually handled and controlled (e.g., by a surgeon performing a surgical procedure on a patient). Alternatively, camera head 502 may be coupled to a manipulator arm of a computer-assisted surgical system. In this configuration, imaging device 102 may be controlled by the computer-assisted surgical system using robotic and/or teleoperation technology.

As shown, an illumination channel 506 may pass through camera head 502 and shaft 504. Illumination channel 506 is configured to provide a conduit for light emitted by illumination system 106 to travel to a scene that is being imaged by imaging device 102.

A distal end 508 of shaft 504 may be positioned at or near a scene that is to be imaged by imaging device 102. For example, distal end 508 of shaft 504 may be inserted into a patient. In this configuration, imaging device 102 may be used to capture images of anatomy and/or other objects within the patient.

Camera 112 and depth sensor 114 may be located anywhere along shaft 504 of imaging device 102. In the example shown in FIG. 5, camera 112 and depth sensor 114 are located at distal end 508 of shaft 504. This configuration may be referred to as a "chip on tip" configuration. Alternatively, camera 112 and/or depth sensor 114 may be located more towards camera head 502 and/or within camera head 502. In these alternative configurations, optics (e.g., lenses, optical fibers, etc.) included in shaft 504 and/or camera head 106 may convey light from a scene to camera 112 and/or depth sensor 114.

In some examples, camera 112 and depth sensor 114 may be staggered at different distances from distal end 508 of shaft 504. By staggering the distances of camera 112 and depth sensor 114 from distal end 508 of shaft 504, imaging device 102 may take on a tapered configuration with a reduced size (e.g., diameter) towards distal end 508 of the shaft 504, which may be helpful for inserting the imaging device 102 into an internal space of a patient.

Figure 6:
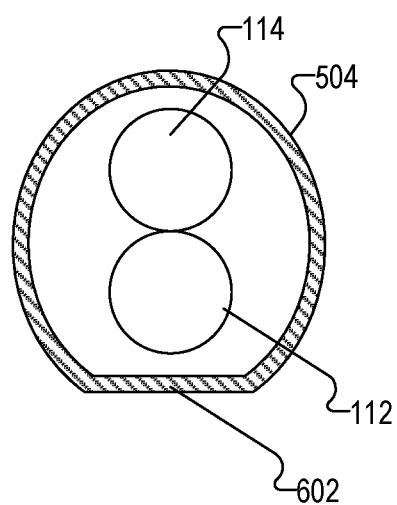
FIG. 6 depicts a cross-sectional view of a shaft of an imaging device according to principles described herein.

FIG. 6 depicts a cross-sectional view of shaft 504 of imaging device 102 taken along lines 6-6 in FIG. 5. As shown, shaft 504 includes a relatively flat bottom surface 602. With reference to this bottom surface 602, depth sensor 114 is positioned above camera 112. Such positioning may allow for a more narrow shaft 504 compared to shafts of conventional imaging devices that have two cameras side-by-side in order to acquire stereoscopic images. It will be recognized that camera 112 and depth sensor 114 may have any suitable relative position within shaft 504 as may serve a particular implementation.

While the examples described herein have shown imaging device 102 as including a single camera 112 in combination with a depth sensor 114, it will be recognized that in some alternative embodiments, imaging device 102 may include multiple cameras 112 and/or multiple depth sensors 114. For example, in some embodiments, imaging device 102 may include two cameras 112 in combination with a single depth sensor 114. In these embodiments, depth data may be generated based on the images acquired by both cameras 112. The depth data generated by depth sensor 114 may be used to fine tune or otherwise enhance the depth data generated based on the images acquired by both cameras 112. However, for purposes of the examples described herein, imaging device 102 includes no more than one camera 112 in combination with depth sensor 114.

Figure 7:
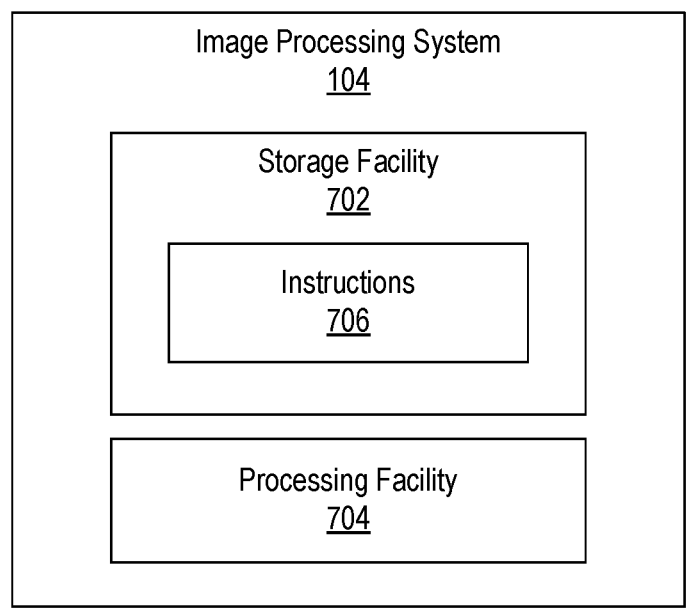
FIG. 7 illustrates exemplary components of image processing system according to principles described herein.

FIG. 7 illustrates exemplary components of image processing system 104. As shown, image processing system 104 may include, without limitation, a storage facility 702 and a processing facility 704 selectively and communicatively coupled to one another. Facilities 702 and 704 may each include or be implemented by hardware and/or software components (e.g., processors, memories, communication interfaces, instructions stored in memory for execution by the processors, etc.). For example, facilities 702 and 704 may be implemented by any component in a computer-assisted surgical system. In some examples, facilities 702 and 704 may be distributed between multiple devices and/or multiple locations as may serve a particular implementation.

Storage facility 702 may maintain (e.g., store) executable data used by processing facility 704 to perform one or more of the operations described herein. For example, storage facility 702 may store instructions 706 that may be executed by processing facility 704 to perform one or more of the operations described herein. Instructions 706 may be implemented by any suitable application, software, code, and/or other executable data instance. Storage facility 702 may also maintain any data received, generated, managed, used, and/or transmitted by processing facility 704.

Processing facility 704 may be configured to perform (e.g., execute instructions 706 stored in storage facility 702 to perform) various operations associated with generating images for display on a display device.

For example, processing facility 704 may receive image data 120 and depth data 122 from camera 112 and depth sensor 114, respectively, and use the received data to generate right-side perspective image 124-R and left-side perspective image 124-L that, when viewed concurrently by a user (e.g., a surgeon), together form a stereoscopic image.

Processing facility 704 may generate right-side perspective image 124-R and left-side perspective image 124-L based on image data 120 and depth data 122 in any suitable manner. For example, based on a position of depth sensor 114, processing facility 704 may determine a position of a virtual right-side camera and a position of a left-side virtual camera. These virtual camera positions may be based on predetermined offsets as specified in a transfer function maintained in storage facility 702 and/or otherwise accessed by processing facility 704. Based on the determined positions of the virtual right-side and left-side cameras and in accordance with the transfer function, processing facility 704 may transform depth data 122 into right-side perspective image 124-R and left-side perspective image 124-L. Processing facility 704 may apply color to each of right-side perspective image 124-R and left-side perspective image 124-L using color information included in image data 120. These operations may be performed in any suitable manner.

Processing facility 704 may be further configured to instruct a first display device to display right-side perspective image 124-R and a second display device to display left-side perspective image 124-L. These perspective images may be displayed concurrently so as to form a stereoscopic image when viewed by a user.

Figure 8:
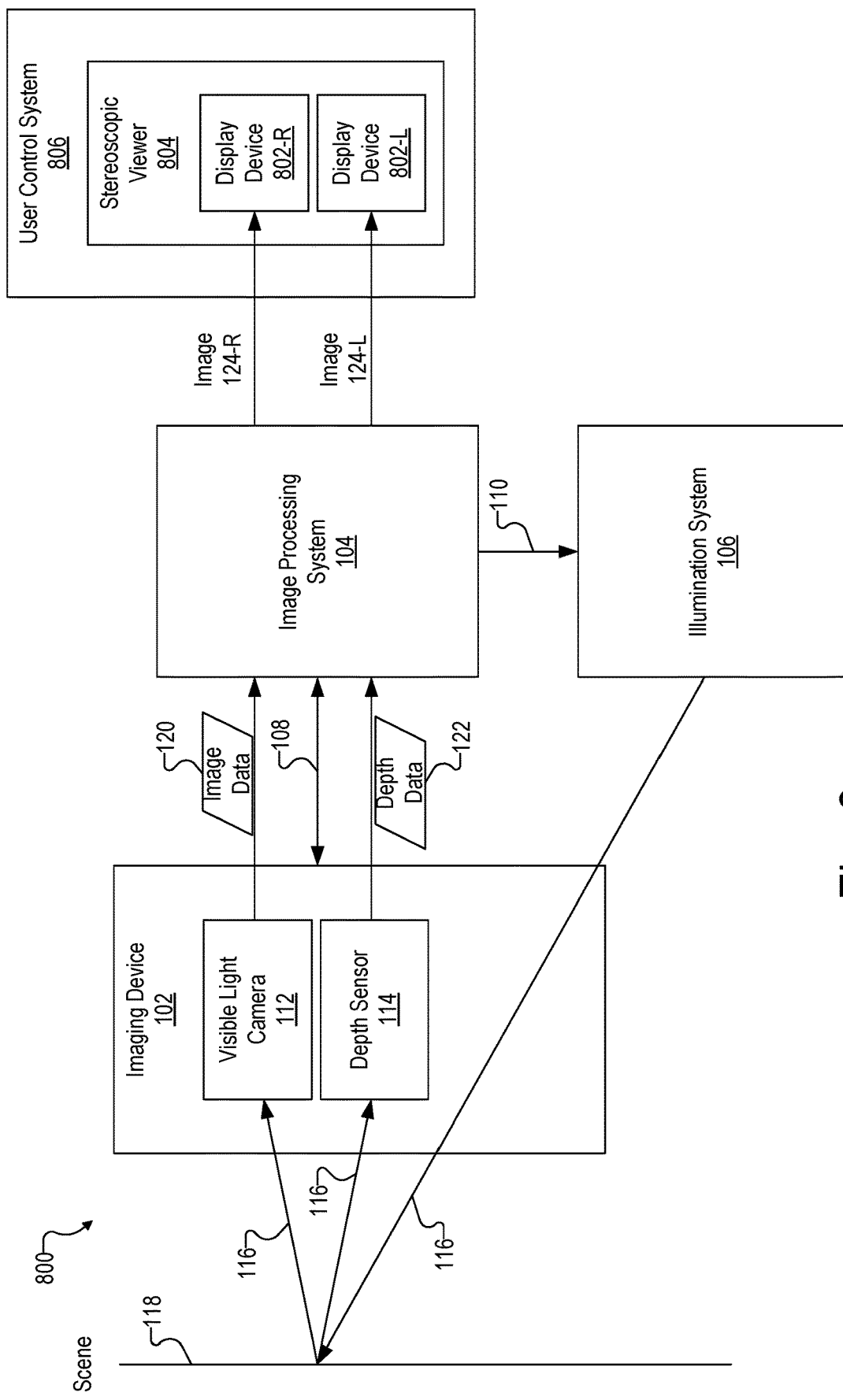
FIG. 8 shows an exemplary configuration in which first and second display devices are integrated into a stereoscopic viewer of a user control system according to principles described herein.

The first and second display devices may be implemented by any suitable type of display device as may serve a particular implementation. To illustrate, FIG. 8 shows an exemplary configuration 800 in which a display device 802-R and a display device 802-L are integrated into a stereoscopic viewer 804 of a user control system 806.

User control system 806 may be implemented by any suitable system configured to be utilized by a user to remotely perform a medical procedure with respect to a patient. An exemplary user control system used in connection with a computer-assisted surgical system is described in more detail below.

Stereoscopic viewer 804 may be configured to facilitate selective viewing by a user's right eye of display device 802-R and the user's left eye of display device 802-L. For example, stereoscopic viewer 804 may be implemented by a headset (e.g., a headset used in virtual and/or augmented reality applications), separate viewing lenses for each eye, and/or any other suitable components as may serve a particular implementation.

As shown, image processing system 104 (e.g., processing facility 704) is configured to transmit right-side perspective image 124-R to display device 802-R, which is configured to render right-side perspective image 124-R in any suitable manner. Likewise, image processing system 104 is configured to transmit left-side perspective image 124-L to display device 802-L, which is configured to render left-side perspective image 124-L in any suitable manner. When a user positions his or her eyes in front of stereoscopic viewer 804, the user's right eye sees only right-side perspective image 124-R while the user's left eye sees only left-side perspective image 124-L. In this manner, the user perceives a stereoscopic image formed by the combination of right-side perspective image 124-R and left-side perspective image 124-L.

Image processing system 104 may be additionally or alternatively configured to perform one or more other operations based on depth data 122 obtained by depth sensor 114. For example, based on depth data 122, image processing system 104 may register the stereoscopic image formed by the combination of right-side perspective image 124-R and left-side perspective image 124-L with a three-dimensional model of anatomy within the scene depicted in the stereoscopic image. Based on this registration, image processing system 104 may direct first and second display devices to display the three-dimensional model together with right-side perspective image 124-R and left-side perspective image 124-L. For example, the three-dimensional model may be overlaid on top of right-side perspective image 124-R and left-side perspective image 124-L in any suitable manner. The three-dimensional model may, in some examples, allow a user to see underlying anatomy (e.g., vasculature and/or other sub-tissue structures) together with the stereoscopic image. Parts of the three-dimensional model may be selectively removed to give the appearance of line-of-sight occlusion by anatomy, depending on depth data in relation to the three-dimensional position of the model.

Other operations that may be performed by image processing system 104 based on depth data 122 include, but are not limited to, distance measurement operations, efficiency-related operations, and tissue deformation measurement operations. Examples of these operations are described in U.S. Provisional Patent Application No. 62/888,115, filed the same day as the present application and entitled "SYSTEMS AND METHODS FOR PERFORMANCE OF DEPTH SENSOR AND AUXILIARY SENSOR-BASED OPERATIONS ASSOCIATED WITH A COMPUTER-ASSISTED SURGICAL SYSTEM," the contents of which are incorporated herein by reference in their entirety.

Figure 9:
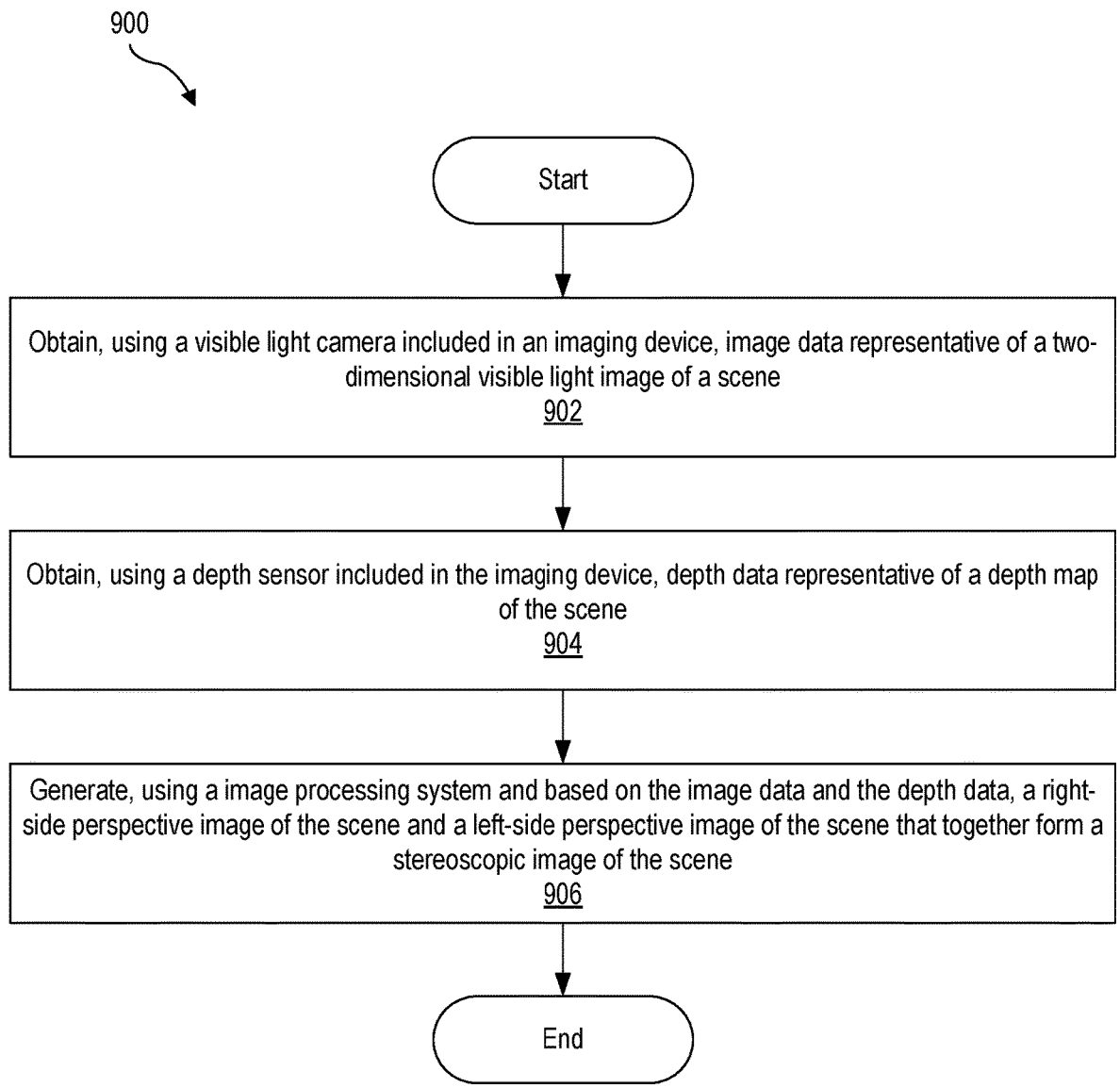
FIG. 9 illustrates an exemplary method according to principles described herein.

FIG. 9 illustrates an exemplary method 900 that may be performed by medical imaging system 100. While FIG. 9 illustrates exemplary operations according to one embodiment, other embodiments may omit, add to, reorder, and/or modify any of the operations shown in FIG. 9.

In operation 902, a visible light camera included in an imaging device is used to obtain image data representative of a two-dimensional visible light image of a scene. Operation 902 may be performed in any of the ways described herein.

In operation 904, a depth sensor included in the imaging device is used to obtain depth data representative of a depth map of the scene. Operation 904 may be performed in any of the ways described herein.

In operation 906, an image processing system is used to generate, based, based on the image data and the depth data, a right-side perspective image of the scene and a left-side perspective image of the scene that together form a stereoscopic image of the scene. Operation 906 may be performed in any of the ways described herein.

The systems and methods described herein may be used in connection with a computer-assisted surgical system used to perform a surgical procedure with respect to a patient. For example, imaging device 102, image processing system 104, and/or illumination system 106 may be used in connection with and/or implemented by a computer-assisted surgical system.

Figure 10:
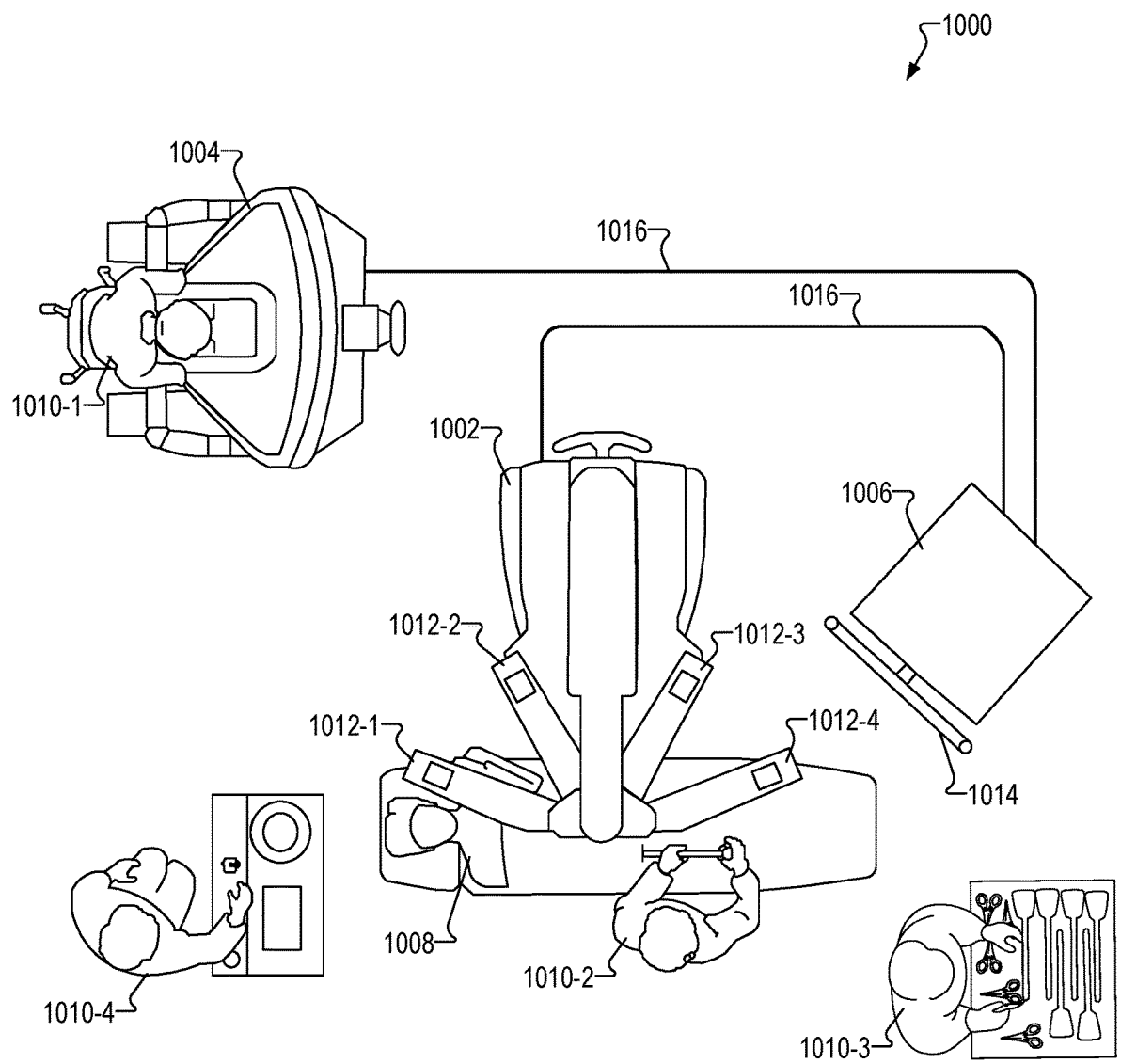
FIG. 10 illustrates an exemplary computer-assisted surgical system according to principles described herein.

FIG. 10 illustrates an exemplary computer-assisted surgical system 1000 ("surgical system 1000"). As shown, surgical system 1000 may include a manipulating system 1002, a user control system 1004, and an auxiliary system 1006 communicatively coupled one to another. Surgical system 1000 may be utilized by a surgical team to perform a computer-assisted surgical procedure on a patient 1008. As shown, the surgical team may include a surgeon 1010-1, an assistant 1010-2, a nurse 1010-3, and an anesthesiologist 1010-4, all of whom may be collectively referred to as "surgical team members 1010." Additional or alternative surgical team members may be present during a surgical session as may serve a particular implementation.

While FIG. 10 illustrates an ongoing minimally invasive surgical procedure, it will be understood that surgical system 1000 may similarly be used to perform open surgical procedures or other types of surgical procedures that may similarly benefit from the accuracy and convenience of surgical system 1000. Additionally, it will be understood that the surgical session throughout which surgical system 1000 may be employed may not only include an operative phase of a surgical procedure, as is illustrated in FIG. 10, but may also include preoperative, postoperative, and/or other suitable phases of the surgical procedure. A surgical procedure may include any procedure in which manual and/or instrumental techniques are used on a patient to investigate or treat a physical condition of the patient.

As shown in FIG. 10, manipulating system 1002 may include a plurality of manipulator arms 1012 (e.g., manipulator arms 1012-1 through 1012-4) to which a plurality of surgical instruments may be coupled. Each surgical instrument may be implemented by any suitable surgical tool (e.g., a tool having tissue-interaction functions), medical tool, imaging device (e.g., an endoscope), sensing instrument (e.g., a force-sensing surgical instrument), diagnostic instrument, or the like that may be used for a computer-assisted surgical procedure on patient 1008 (e.g., by being at least partially inserted into patient 1008 and manipulated to perform a computer-assisted surgical procedure on patient 1008). While manipulating system 1002 is depicted and described herein as including four manipulator arms 1012, it will be recognized that manipulating system 1002 may include only a single manipulator arm 1012 or any other number of manipulator arms as may serve a particular implementation.

Manipulator arms 1012 and/or surgical instruments attached to manipulator arms 1012 may include one or more displacement transducers, orientational sensors, and/or positional sensors used to generate raw (i.e., uncorrected) kinematics information. One or more components of surgical system 1000 may be configured to use the kinematics information to track (e.g., determine positions of) and/or control the surgical instruments.

User control system 1004 may be configured to facilitate control by surgeon 1010-1 of manipulator arms 1012 and surgical instruments attached to manipulator arms 1012. For example, surgeon 1010-1 may interact with user control system 1004 to remotely move or manipulate manipulator arms 1012 and the surgical instruments. To this end, user control system 1004 may provide surgeon 1010-1 with imagery (e.g., high-definition 3D imagery) of a surgical area associated with patient 1008 as captured by an imaging system (e.g., any of the medical imaging systems described herein). In certain examples, user control system 1004 may include a stereo viewer having two displays where stereoscopic images of a surgical area associated with patient 1008 and generated by a stereoscopic imaging system may be viewed by surgeon 1010-1. Surgeon 1010-1 may utilize the imagery to perform one or more procedures with one or more surgical instruments attached to manipulator arms 1012.

To facilitate control of surgical instruments, user control system 1004 may include a set of master controls. These master controls may be manipulated by surgeon 1010-1 to control movement of surgical instruments (e.g., by utilizing robotic and/or teleoperation technology). The master controls may be configured to detect a wide variety of hand, wrist, and finger movements by surgeon 1010-1. In this manner, surgeon 1010-1 may intuitively perform a procedure using one or more surgical instruments. In some examples, user control system 1004 implements user control system 806.

Auxiliary system 1006 may include one or more computing devices configured to perform primary processing operations of surgical system 1000. In such configurations, the one or more computing devices included in auxiliary system 1006 may control and/or coordinate operations performed by various other components (e.g., manipulating system 1002 and user control system 1004) of surgical system 1000. For example, a computing device included in user control system 1004 may transmit instructions to manipulating system 1002 by way of the one or more computing devices included in auxiliary system 1006. As another example, auxiliary system 1006 may receive, from manipulating system 1002, and process image data representative of imagery captured by an imaging device attached to one of manipulator arms 1012.

In some examples, auxiliary system 1006 may be configured to present visual content to surgical team members 1010 who may not have access to the images provided to surgeon 1010-1 at user control system 1004. To this end, auxiliary system 1006 may include a display monitor 1014 configured to display one or more user interfaces, such as images (e.g., 2D images, 3D images) of the surgical area, information associated with patient 1008 and/or the surgical procedure, and/or any other visual content as may serve a particular implementation. For example, display monitor 1014 may display images of the surgical area together with additional content (e.g., graphical content, contextual information, etc.) concurrently displayed with the images. In some embodiments, display monitor 1014 is implemented by a touchscreen display with which surgical team members 1010 may interact (e.g., by way of touch gestures) to provide user input to surgical system 1000.

Manipulating system 1002, user control system 1004, and auxiliary system 1006 may be communicatively coupled one to another in any suitable manner. For example, as shown in FIG. 10, manipulating system 1002, user control system 1004, and auxiliary system 1006 may be communicatively coupled by way of control lines 1016, which may represent any wired or wireless communication link as may serve a particular implementation. To this end, manipulating system 1002, user control system 1004, and auxiliary system 1006 may each include one or more wired or wireless communication interfaces, such as one or more local area network interfaces, Wi-Fi network interfaces, cellular interfaces, etc.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 11:
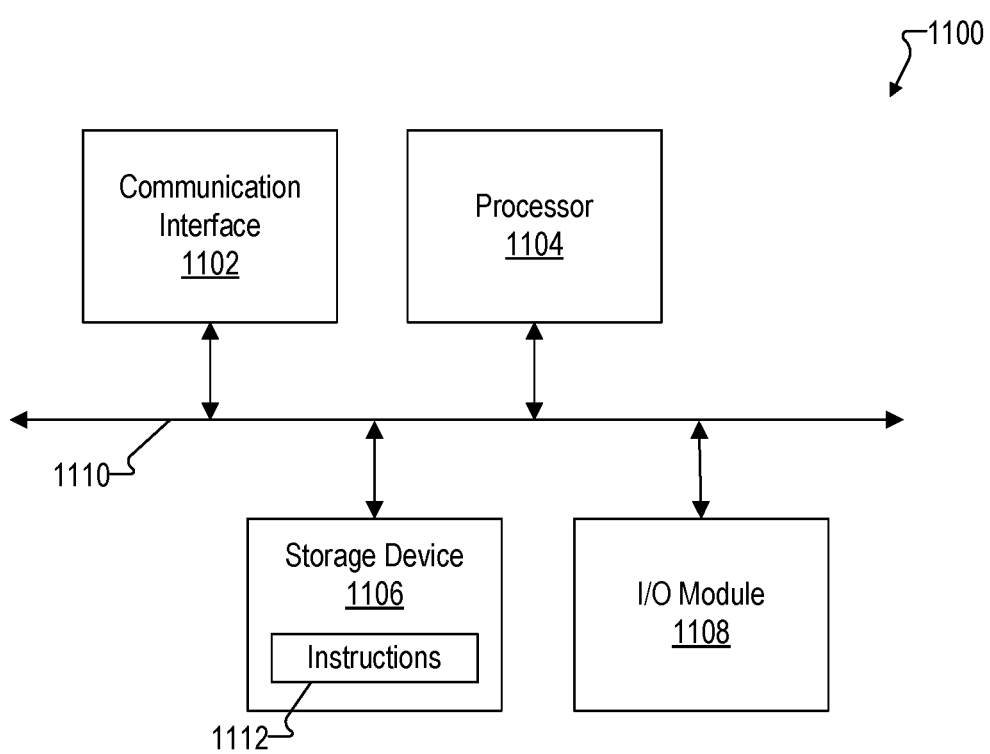
FIG. 11 illustrates an exemplary computing device according to principles described herein.

FIG. 11 illustrates an exemplary computing device 1100 that may be specifically configured to perform one or more of the processes described herein. Any of the systems, computing devices, and/or other components described herein may be implemented by computing device 1100.

As shown in FIG. 11, computing device 1100 may include a communication interface 1102, a processor 1104, a storage device 1106, and an input/output ("I/O") module 1108 communicatively connected one to another via a communication infrastructure 1110. While an exemplary computing device 1100 is shown in FIG. 11, the components illustrated in FIG. 11 are not intended to be limiting. Additional or alternative components may be used in other embodiments. Components of computing device 1100 shown in FIG. 11 will now be described in additional detail.

Communication interface 1102 may be configured to communicate with one or more computing devices. Examples of communication interface 1102 include, without limitation, a wired network interface (such as a network interface card), a wireless network interface (such as a wireless network interface card), a modem, an audio/video connection, and any other suitable interface.

Processor 1104 generally represents any type or form of processing unit capable of processing data and/or interpreting, executing, and/or directing execution of one or more of the instructions, processes, and/or operations described herein. Processor 1104 may perform operations by executing computer-executable instructions 1112 (e.g., an application, software, code, and/or other executable data instance) stored in storage device 1106.

Storage device 1106 may include one or more data storage media, devices, or configurations and may employ any type, form, and combination of data storage media and/or device. For example, storage device 1106 may include, but is not limited to, any combination of the non-volatile media and/or volatile media described herein. Electronic data, including data described herein, may be temporarily and/or permanently stored in storage device 1106. For example, data representative of computer-executable instructions 1112 configured to direct processor 1104 to perform any of the operations described herein may be stored within storage device 1106. In some examples, data may be arranged in one or more databases residing within storage device 1106.

I/O module 1108 may include one or more I/O modules configured to receive user input and provide user output. I/O module 1108 may include any hardware, firmware, software, or combination thereof supportive of input and output capabilities. For example, I/O module 1108 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1108 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1108 is configured to provide graphical data to a display for presentation to a user. The graphical data may be representative of one or more graphical user interfaces and/or any other graphical content as may serve a particular implementation.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A medical imaging system, comprising:
an imaging device that includes
a visible light camera configured to obtain image data representative of a two-dimensional visible light image of a scene; and
a depth sensor separate from the visible light camera and configured to obtain depth data representative of a depth map of the scene; and
an image processing system communicatively coupled to the imaging device and configured to:
generate, based on the image data and the depth data, a right-side perspective image of the scene and a left-side perspective image of the scene that together form a stereoscopic image of the scene;
instruct a first display device to display the right-side perspective image of the scene and a second display device to display the left-side perspective image of the scene,
register, based on the depth data, the stereoscopic image of the scene with a three-dimensional model of anatomy within the scene, and
direct the first and second display devices to display, based on the registering, the three-dimensional model together with the right-side and left-side perspective images of the scene.

2. The medical imaging system of claim 1, wherein the visible light camera comprises a single visible light camera.

3. The medical imaging system of claim 1, further comprising:
a first illumination source configured to emit visible light;
wherein the visible light camera is configured to obtain the image data using light by
detecting the visible light after the visible light reflects off a surface within the scene, and
generating, based on the detected visible light, the image data.

4. The medical imaging system of claim 3, wherein the depth sensor is configured to obtain the depth data by:
detecting the visible light after the visible light reflects off the surface within the scene; and
generating, based on the detected visible light, the depth data.

5. The medical imaging system of claim 3, further comprising:
a second illumination source configured to emit non-visible light;
wherein the depth sensor is configured to obtain the depth data by detecting the non-visible light after the non-visible light reflects off the surface within the scene; and
generating, based on the detected non-visible light, the depth data.

6. The medical imaging system of claim 1, wherein, with respect to a bottom surface of a shaft of the imaging device, the depth sensor is positioned above the visible light camera.

7. The medical imaging system of claim 1, wherein the first display device and the second display device are integrated into a stereoscopic viewer of a user control system utilized by a user to remotely perform a medical procedure with respect to a patient.

8. The medical imaging system of claim 1, wherein:
the imaging device is an endoscope configured to be inserted into a patient; and
the scene includes an internal space within the patient.

9. The medical imaging system of claim 1, wherein:
the imaging device comprises a camera head and a shaft extending from the camera head; and
the visible light camera and the depth sensor are disposed within the camera head or the shaft.

10. A system comprising:
an imaging device comprising
a visible light camera configured to obtain image data representative of a two-dimensional visible light image of a scene; and
a depth sensor configured to obtain depth data representative of a depth map of the scene;
an image processing system communicatively coupled to the imaging device and configured to generate, based on the image data and the depth data, a right-side perspective image of the scene and a left-side perspective image of the scene that together form a stereoscopic image of the scene; and
a user control system communicatively coupled to the image processing system and configured to facilitate remote performance by a user of a medical procedure with respect to a patient, the user control system comprising a stereoscopic viewer that comprises:
a first display device configured to display the right-side perspective image of the scene; and
a second display device configured to display the left-side perspective image of the scene;
wherein the image processing system is further configured to:
register, based on the depth data, the stereoscopic image of the scene with a three-dimensional model of anatomy within the scene, and
direct the first and second display devices to display, based on the registering, the three-dimensional model together with the right-side and left-side perspective images of the scene.

11. The system of claim 10, wherein the visible light camera comprises a single visible light camera.

12. The system of claim 10, further comprising:
a first illumination source configured to emit visible light;
wherein the visible light camera is configured to obtain the image data using light by
detecting the visible light after the visible light reflects off a surface within the scene, and
generating, based on the detected visible light, the image data.

13. The system of claim 12, wherein the depth sensor is configured to obtain the depth data by:
detecting the visible light after the visible light reflects off the surface within the scene; and generating, based on the detected visible light, the depth data.

14. The system of claim 12, further comprising:
a second illumination source configured to emit non-visible light;
wherein the depth sensor is configured to obtain the depth data by
   detecting the non-visible light after the non-visible light reflects off the surface within the scene; and
   generating, based on the detected non-visible light, the depth data.

15. The system of claim 10, wherein, with respect to a bottom surface of a shaft of the imaging device, the depth sensor is positioned above the visible light camera.

16. The system of claim 10, wherein the first display device and the second display device are integrated into a stereoscopic viewer of a user control system configured to be utilized by a user to remotely perform a medical procedure with respect to a patient.

17. The system of claim 10, wherein:
the imaging device is an endoscope configured to be inserted into a patient; and
the scene includes an internal space within the patient.

18. The system of claim 10, wherein:
the imaging device comprises a camera head and a shaft extending from the camera head; and
the visible light camera and the depth sensor are disposed within the camera head or the shaft.

* * * * *